US010772883B2

(12) United States Patent
Grant et al.

(10) Patent No.: US 10,772,883 B2
(45) Date of Patent: *Sep. 15, 2020

(54) DIKETOPIPERAZINE MICROPARTICLES WITH DEFINED SPECIFIC SURFACE AREAS

(71) Applicant: MannKind Corporation, Valencia, CA (US)

(72) Inventors: Marshall L. Grant, Newtown, CT (US); Grayson W. Stowell, Cary, NC (US); Paul Menkin, Branford, CT (US); John J. Freeman, Jr., New Fairfield, CT (US)

(73) Assignee: MannKind Corporation, Westlake Village, CA (US)

( * ) Notice: Subject to any disclaimer, the term of this patent is extended or adjusted under 35 U.S.C. 154(b) by 41 days.

This patent is subject to a terminal disclaimer.

(21) Appl. No.: 15/462,559

(22) Filed: Mar. 17, 2017

(65) Prior Publication Data

US 2017/0189395 A1 Jul. 6, 2017

Related U.S. Application Data

(60) Continuation of application No. 14/251,513, filed on Apr. 11, 2014, now Pat. No. 9,630,930, which is a division of application No. 13/377,682, filed as application No. PCT/US2010/038298 on Jun. 11, 2010, now Pat. No. 8,734,845.

(60) Provisional application No. 61/186,773, filed on Jun. 12, 2009.

(51) Int. Cl.

| | |
|---|---|
| ***A61K 31/495*** | (2006.01) |
| ***A61K 9/00*** | (2006.01) |
| ***A61K 9/16*** | (2006.01) |
| ***A61K 9/19*** | (2006.01) |
| ***A61K 9/14*** | (2006.01) |
| ***A61K 38/28*** | (2006.01) |
| ***A61K 45/06*** | (2006.01) |
| ***A61M 15/00*** | (2006.01) |
| ***C07D 241/08*** | (2006.01) |
| ***A61K 31/5575*** | (2006.01) |
| ***A61K 38/19*** | (2006.01) |
| *A61K 38/00* | (2006.01) |

(52) U.S. Cl.

CPC .......... *A61K 31/495* (2013.01); *A61K 9/0075* (2013.01); *A61K 9/145* (2013.01); *A61K 9/1617* (2013.01); *A61K 9/1694* (2013.01); *A61K 9/19* (2013.01); *A61K 31/5575* (2013.01); *A61K 38/193* (2013.01); *A61K 38/28* (2013.01); *A61K 45/06* (2013.01); *A61M 15/0028* (2013.01); *A61M 15/0091* (2013.01); *C07D 241/08* (2013.01); *A61K 38/00* (2013.01); *Y10T 428/2982* (2015.01)

(58) Field of Classification Search

None

See application file for complete search history.

(56) References Cited

U.S. PATENT DOCUMENTS

| | | | | |
|---|---|---|---|---|
| 4,539,131 | A * | 9/1985 | Garner-Gray | C11D 3/3942 252/186.3 |
| 8,551,528 | B2 * | 10/2013 | Grant | A61K 9/0075 424/489 |
| 8,636,001 | B2 * | 1/2014 | Smutney | A61M 15/0028 128/203.15 |
| 8,734,845 | B2 * | 5/2014 | Grant | A61K 9/0075 424/489 |
| 8,778,403 | B2 * | 7/2014 | Grant | A61K 9/0075 424/489 |
| 9,278,902 | B2 | 3/2016 | Tang et al. | |
| 9,278,903 | B2 | 3/2016 | Tang et al. | |
| 9,289,388 | B2 | 3/2016 | Guarnieri | |
| 9,364,436 | B2 * | 6/2016 | Grant | A61K 9/0075 |
| 9,381,243 | B2 | 7/2016 | Johansson et al. | |
| 9,498,437 | B2 | 11/2016 | Chaudry | |
| 9,504,663 | B2 | 11/2016 | Freissmuth et al. | |
| 9,630,930 | B2 * | 4/2017 | Grant | A61K 9/0075 |
| 9,713,599 | B2 | 7/2017 | Wade | |
| 9,758,465 | B2 | 9/2017 | Laing | |
| 2004/0105819 | A1 | 6/2004 | Hale et al. | |
| 2004/0241232 | A1 * | 12/2004 | Brown | A61K 9/0075 424/469 |
| 2007/0111983 | A1 | 5/2007 | Fong | |
| 2008/0200449 | A1 | 8/2008 | Olschewski et al. | |
| 2008/0226736 | A1 | 9/2008 | Caponetti et al. | |
| 2009/0036465 | A1 | 2/2009 | Roscigno et al. | |
| 2010/0048693 | A1 | 2/2010 | Geraci et al. | |
| 2012/0177693 | A1 | 7/2012 | Cipolla et al. | |
| 2013/0039847 | A1 | 2/2013 | Gessler et al. | |
| 2013/0040898 | A1 | 2/2013 | Johansson | |
| 2013/0261177 | A1 | 10/2013 | Johansson et al. | |
| 2014/0044797 | A1 | 2/2014 | Johansson et al. | |
| 2015/0057325 | A1 | 2/2015 | Johansson et al. | |
| 2015/0196516 | A1 | 7/2015 | Yacoub et al. | |
| 2016/0175319 | A1 | 6/2016 | Freissmuth et al. | |

FOREIGN PATENT DOCUMENTS

| | | | | |
|---|---|---|---|---|
| WO | WO-2009006558 | A1 * | 1/2009 | A61L 27/3817 |
| WO | 2012107364 | A1 | 8/2012 | |

(Continued)

OTHER PUBLICATIONS

Kumar et al., "A Comprehensive Review of Treprostinil Pharmacokinetics via Four Routes of Administration", Clin Pharmacokinet, 2016, vol. 55, pp. 1495-1504.

(Continued)

*Primary Examiner* — Dennis J Parad

(74) *Attorney, Agent, or Firm* — K&L Gates LLP; Louis C. Cullman; Hal Gibson

(57) ABSTRACT

Disclosed herein are diketopiperazine microparticles having a specific surface area of less than about 67 $m^2/g$. The diketopiperazine microparticle can be fumaryl diketopiperazine and can comprise a drug such as insulin.

12 Claims, 7 Drawing Sheets

(56) References Cited

FOREIGN PATENT DOCUMENTS

| | | | |
|---|---|---|---|
| WO | 2014085813 | A1 | 6/2014 |
| WO | 2015138423 | A1 | 9/2015 |
| WO | 2016120311 | A1 | 8/2016 |
| WO | 2017192993 | A1 | 11/2017 |

OTHER PUBLICATIONS

Takatsuki et al., "Acute Pulmonary Vasodilator Testing With Inhaled Treprostinil in Children With Pulmonary Arterial Hypertension", Pediatr Cardiol. Apr. 2013 ; vol. 34(4): pp. 1-12.

Aradigm, "ARD-1550 and 1500—Treprostinil for the Treatment of Pulmonary Arterial Hypertension", 2013, http://www.aradigm.com/products_1500.html, p. 1.

Cipolla et al., "Deeper Lung Pulmonary Delivery of Treprostinil is Associated with Delayed Systemic Absorption", Aradigm Corp., p. 1.

Voswinckel et al., "Favorable Effects of Inhaled Treprostinil in Severe Pulmonary Hypertension: Results From Randomized Controlled Pilot Studies", Journal of the American College of Cardiology, vol. 48, No. 8, 2006, pp. 1672-1781.

Patel et al., "In Vitro Delivery of Aerosolized Treprostinil via Modern Mechanical Ventilation", Journal of Aerosol Medicine and Pulmonary Drug Delivery, vol. 26, No. 0, 2013, pp. 1-8.

Hill et al., "Inhaled Therapies for Pulmonary Hypertension", Respiratory Care, Jun. 2015, vol. 60, No. 6, pp. 794-805.

Parker et al., "Inhaled Treprostinil Drug Delivery During Mechanical Ventilation and Spontaneous Breathing Using Two Different Nebulizers", Pediatr Crit Care Med. Jun. 2017 ; 18(6), pp. 1-16.

Poms et al.,"Inhaled Treprostinil for the Treatment of Pulmonary Arterial Hypertension", CriticalCareNurse, vol. 31, No. 6, Dec. 2011, pp. 1-12.

Gupta et al., "Inhaled treprostinil sodium for pulmonary hypertension", Expert Opinion on Orphan Drugs, 2:3, pp. 283-291 (2014).

Ferrantino et al., "Inhaled treprostinil sodium for the treatment of pulmonary arterial hypertension", Expert Opin. Pharmacother, 2011, 12(16), pp. 2583-2593.

Huckaby et al., "Inhaled treprostinil via the Tyvaso Inhalation System through a tracheostomy", BMJ Case Rep 2015. doi:10, pp. 1-3.

Channick et al., "Inhaled treprostinil: a therapeutic review", Drug Design, Development and Therapy 2012, vol. 6 pp. 19-28.

Voswinckel et al., "Metered dose inhaler delivery of treprostinil for the treatment of pulmonary hypertension", Pulmonary Pharmacology & Therapeutics, vol. 22, 2009, pp. 50-56.

Madonna et al., "Pathways and Drugs in Pulmonary ArterialHypertension—Focus on the Role of Endothelin Receptor Antagonists", Cardiovasc Drugs Ther, Jul. 7, 2015, pp. 1-11.

Sandifer et al., "Potent effects of aerosol compared with intravenous treprostinil on the pulmonary circulation", J Appl Physiol 99, Sep. 1, 2005, pp. 2363-2368.

Channick et al., "Safety and Efficacy of Inhaled Treprostinil as Add-On Therapy to Bosentan in Pulmonary Arterial Hypertension", Journal of the American College of Cardiology, vol. 48, No. 7, 2006, pp. 1433-1437.

Zeenat Safdar, "Treatment of pulmonary arterial hypertension: The role of prostacyclin and prostaglandin analogs", respiratory Medicine (2011) 105, pp. 818-827.

* cited by examiner

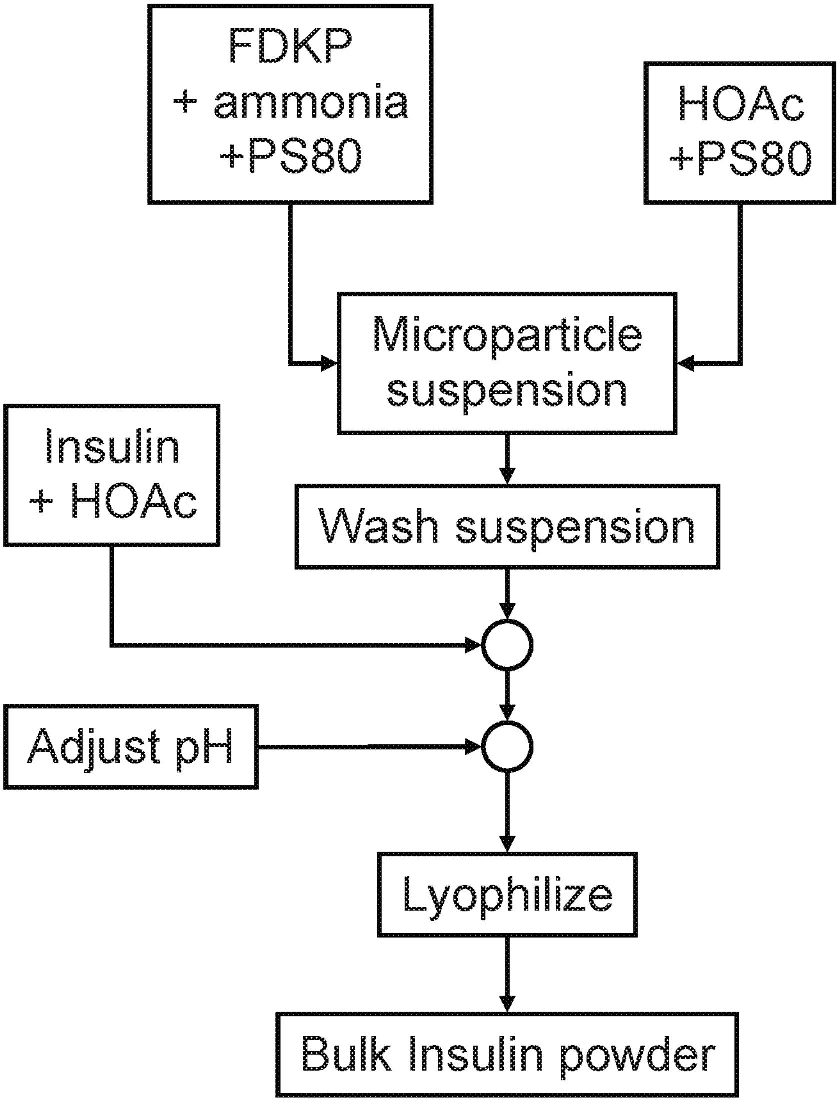

FIG. 3

```
        ┌─────────────┐
        │    FDKP     │
        │  + ammonia  │      ┌─────────┐
        │    +PS80    │      │  HOAc   │
        └──────┬──────┘      │  +PS80  │
               │             └────┬────┘
               ▼                  ▼
        ┌─────────────────────────┐
        │   Microparticle         │
        │    suspension           │
        └────────────┬────────────┘
                     ▼
┌──────────┐   ┌─────────────────┐
│ Insulin  │   │ Wash suspension │
│ + HOAc   │   └────────┬────────┘
└─────┬────┘            │
      │         ○◄──────┘
      └────────►│
                ▼
┌──────────┐   ○
│Adjust pH ├──►│
└──────────┘   ▼
        ┌─────────────┐
        │  Lyophilize │
        └──────┬──────┘
               ▼
        ┌──────────────────┐
        │Bulk Insulin powder│
        └──────────────────┘
```

Regression equation (significant terms only):
$Y = 35.79 + 1.79A - 2.16B + 0.59C + 0.10A^2$ A: ΔFDKP (%)
B: $\Delta NH_4OH$ (%)
C: ΔHOAc (%)

Standard error of prediction: ±2.0 $m^2/g$

Regression equation (significant terms only):
$Y = 44.86 + 1.49A - 1.28B + 0.55C$ A: ΔFDKP (%)
B: $\Delta NH_4OH$ (%)
C: ΔHOAc (%)

Standard error of prediction: ±5.6 $m^2/g$

DIKETOPIPERAZINE MICROPARTICLES WITH DEFINED SPECIFIC SURFACE AREAS

CROSS REFERENCE TO RELATED APPLICATIONS

This application is a continuation application of U.S. patent application Ser. No. 14/251,513, filed Apr. 11, 2014, which is a divisional application of U.S. patent application Ser. No. 13/377,682, filed Feb. 2, 2012, which is a 371 of PCT/US2010/038298, filed Jun. 11, 2010, which claims benefit under 35 U.S.C. § 119(e) from U.S. Provisional Patent Application Ser. No. 61/186,773, filed Jun. 12, 2009, the contents of which are incorporated herein by reference in their entirety.

TECHNICAL FIELD

Disclosed herein are diketopiperazine microparticles having a specific surface area of less than about 67 $m^2/g$. The FDKP microparticles can be used as a delivery system for drugs or active agents in the treatment of disease or disorders, for example, those of endocrine origin, including, diabetes and obesity.

BACKGROUND

Delivery of drugs has been a major problem for many years, particularly when the compound to be delivered is unstable under the conditions encountered in the gastro-intestinal tract when administered orally to a subject, prior to reaching its targeted location. For example, it is preferable in many cases to administer drugs orally, especially in terms of ease of administration, patient compliance, and decreased cost. However, many compounds are ineffective or exhibit low or variable potency when administered orally. Presumably this is because the drugs are unstable to conditions in the digestive tract or because they are inefficiently absorbed.

Due to the problems associated with oral drug delivery, drug delivery to the lungs has been explored. For example, typically drugs delivered to the lungs are designed to have an effect on the tissue of the lungs, for example, vasodilators, surfactants, chemotherapeutic agents or vaccines for flu or other respiratory illnesses. Other drugs, including nucleotide drugs, have been delivered to the lungs because they represent a tissue particularly appropriate for treatment, for example, for genetic therapy in cystic fibrosis, where retroviral vectors expressing a defective adenosine deaminase are administered to the lungs.

Drug delivery to the lungs for agents having systemic effects can also be performed. Advantages of the lungs for delivery of systemic agents include the large surface area and the ease of uptake by the lung's mucosal surface. One problem associated with all of these forms of pulmonary drug delivery is that it is difficult to deliver drugs into the lungs due to problems in getting the drugs past all of the natural barriers, such as the cilia lining the trachea, and in trying to administer a uniform volume and weight of drug.

Accordingly, there is room for improvement in the pulmonary delivery of drugs.

SUMMARY

The present disclosure provides systems, microparticles and methods that allow for improved delivery of drugs to the lungs. Embodiments disclosed herein achieve improved delivery by providing diketopiperazine (DKP) microparticles having a specific surface area (SSA) of between about 35 $m^2/g$ and about 67 $m^2/g$. DKP microparticles having a specific surface area in this range exhibit characteristics beneficial to delivery to the lungs such as improved aerodynamic performance and improved drug adsorption.

One embodiment disclosed herein comprises diketopiperazine microparticles having a specific surface area of less than about 67 $m^2/g$. Another embodiment includes diketopiperazine microparticles in which the specific surface area is from about 35 $m^2/g$ to about 67 $m^2/g$. Another embodiment includes diketopiperazine microparticles in which the specific surface area is greater than about 35 $m^2/g$ in the absence of active agent but less than about 62 $m^2/g$ after the active agent is adsorbed to the particles.

In another embodiment, the fumaryl diketopiperazine (FDKP) microparticles having a specific surface area ranging from about 35 $m^2/g$ to about 67 $m^2/g$ comprise a drug or active agent, wherein the stated SSA is determined prior to addition of drug to the particle. Binding of an active agent onto the particle tends to reduce SSA. In various embodiments of the FDKP microparticles, the drug can be, for example, a peptide, or a protein, including, endocrine hormones, for example, insulin, glucagon-like peptide-1 (GLP-1), glucagon, exendin, parathyroid hormone, obestatin, calcitonin, oxyntomodulin, and the like. Another embodiment of the FDKP microparticles having a specific surface area ranging from about 35 $m^2/g$ to about 67 $m^2/g$ can include a drug/peptide content that can vary depending on downstream conditions of the synthetic process for making the microparticles. In a particular example, the FDKP microparticles can be prepared to have drug/peptide content that can vary depending on the dose to be targeted or delivered. For example, wherein the drug is insulin, the insulin component can be from about 3 U/mg to about 4 U/mg in the powder formulation comprising the microparticles. In certain embodiments, the drug is adsorbed to the surfaces of the microparticles. In further embodiments of such drug loaded microparticles the SSA of the drug loaded microparticles is less than about 62 $m^2/g$.

Embodiments disclosed herein also include dry powders comprising the microparticles. In one embodiment, the dry powders comprise FDKP microparticles having a specific surface area of less than about 67 $m^2/g$. Another embodiment includes diketopiperazine microparticles in which the specific surface area is from about 35 $m^2/g$ to about 67 $m^2/g$. Another embodiment includes diketopiperazine microparticles comprising a drug or active agent in which the specific surface area is from about 35 $m^2/g$ to about 62 $m^2/g$.

In embodiments of the dry powders, the FDKP microparticles comprise a drug. In another embodiment of the dry powders, the drug is a peptide of various molecular size or mass, including; insulin, glucagon-like peptide-1, glucagon, exendin, parathyroid hormone, calcitonin, oxyntomodulin, and the like. In one of these embodiments of the dry powders, wherein the drug is insulin, the insulin content of the FDKP microparticles is from about 3 U/mg to about 4 U/mg.

Further embodiments concern drug delivery systems comprising an inhaler, a unit dose dry powder medicament container, for example, a cartridge, and a powder formulation comprising the microparticles disclosed herein and an active agent. In one embodiment, the drug delivery system for use with the dry powders includes an inhalation system comprising a high resistance inhaler having air conduits that impart a high resistance to airflow through the conduits for deagglomerating and dispensing the powder formulation. In one embodiment, the inhalation system has a resistance value of, for example, from approximately 0.065 (√kPa)/liter per minute to about 0.200 (√kPa)/liter per minute. In certain embodiments, the dry powders can be delivered effectively by inhalation with an inhalation system wherein the peak inhalation pressure differential can range from about 2 kPa to about 20 kPa, which can produce resultant peak flow rates of about between 7 and 70 liters per minute. In certain embodiments, the inhalation systems are configured to provide a single dose by discharging powder from the inhaler as a continuous flow, or as one or more pulses of powder delivered to a patient. In some embodiments disclosed herewith, the dry powder inhalation system comprises a predetermined mass flow balance within the inhaler. For example, a flow balance of approximately 10% to 70% of the total flow exiting the inhaler and into the patient is delivered by one or more dispensing ports, which allows airflow to pass through the area containing the powder formulation, and wherein approximately 30% to 90% of the air flow is generated from other conduits of the inhaler. Moreover, bypass flow, or flow not entering and exiting the area of powder containment such as through a cartridge, can recombine with the flow exiting the powder dispensing port within the inhaler to dilute, accelerate and ultimately deagglomerate the fluidized powder prior to exiting the inhaler mouthpiece. In one embodiment, inhaler system flow rates ranging from about 7 to 70 liters per minute result in greater than 75% of the container powder content or the cartridge powder content dispensed in fill masses between 1 and 30 mg. In certain embodiments, an inhalation system as described above can emit a respirable fraction/fill of a powder dose at percentages greater than 40% in a single inhalation, greater than 50%, greater than 60%, or greater than 70%.

In particular embodiments, an inhalation system is provided comprising a dry powder inhaler, a dry powder formulation comprising microparticles of fumaryl diketopiperazine, wherein the unloaded FDKP microparticles have a specific surface area of less than about 67 $m^2/g$ and one or more than one active agents. In some aspects of this embodiment of the inhalation system, the dry powder formulation is provided in a unit dose cartridge. Alternatively, the dry powder formulation can be preloaded or prefilled in the inhaler. In this embodiment, the structural configuration of the inhalation system allows for the deagglomeration mechanism of the inhaler to produce respirable fractions greater than 50%; that is, more than half of the powder contained in the inhaler (cartridge) is emitted as particles of less than 5.8 μm. In one embodiment, the inhalers can discharge greater than 85% of a powder medicament contained within a container during dosing. In certain embodiments, the inhalers can discharge greater than 85% of a powder medicament contained in a single inhalation. In certain embodiments, the inhalers can discharge greater that 90% of the cartridge contents or container contents in less than 3 seconds at pressure differentials between 2 kPa and 5 kPa with fill masses ranging up to 30 mg.

Embodiments disclosed herein also include methods. In one embodiment, a method of treating an endocrine-related disease or disorder comprising administering to a person in need thereof a dry powder formulation comprising FDKP microparticles having a specific surface area of less than about 67 $m^2/g$ and a drug suitable to treat said disease or disorder. Another embodiment includes diketopiperazine microparticles in which the specific surface area is from about 35 $m^2/g$ to about 67 $m^2/g$. Another embodiment includes diketopiperazine microparticles comprising an active in which the specific surface area is less than about 62 $m^2/g$. One embodiment includes a method of treating an insulin-related disorder comprising administering a dry powder comprising microparticles of FDKP described above to a person in need thereof. The method comprises administering to a subject a dry powder formulation comprising microparticles of fumaryl diketopiperazine having an SSA in the above cited ranges. In various embodiments an insulin-related disorder can specifically include or exclude any or all of pre-diabetes, type 1 diabetes mellitus (honeymoon phase, post-honeymoon phase, or both), type 2 diabetes mellitus, gestational diabetes, hypoglycemia, hyperglycemia, insulin resistance, secretory dysfunction, impaired early-phase release of insulin, loss of pancreatic β-cell function, loss of pancreatic β-cells, and metabolic disorder. In one embodiment, the dry powder comprises insulin. In other embodiments, the dry powder comprises glucagon, an exendin, or GLP-1.

Other embodiments disclosed herein include methods of making microparticles suitable for pulmonary administration as a dry powder. In one embodiment, the method includes forming diketopiperazine microparticles with a specific surface area of about 35 $m^2/g$ to about 67 $m^2/g$ within a 95% confidence limit by adjusting manufacturing conditions to target production of microparticles with a specific surface area of about 52 $m^2/g$. In another embodiment, the adjusting manufacturing conditions comprises increasing or decreasing the temperature or concentration of the ammonia, acetic acid and/or diketopiperazine in a feed solution.

Another embodiment disclosed herein includes a method of making microparticles suitable for pulmonary administration as a dry powder comprising a diketopiperazine such as FDKP. In an embodiment, the microparticles comprise synthesizing an FDKP compound or composition, wherein the microparticles have a surface area from about 35 $m^2/g$ to about 67 $m^2/g$, and determining the surface area of the FDKP microparticles to assess that the surface area in $m^2/g$ using a standard surface area analyzer. In other embodiments, specific surface area is determined after adsorption of active agent to the microparticle instead of or in addition to the determination prior to active agent addition; SSA is less than about 62 $m^2/g$. In one embodiment, the FDKP synthesis comprises: a) dissolving an FDKP composition in a solution having a basic pH to form an FDKP solution; b) providing a solution of a volatile acid, and c) mixing the FDKP solution with the solution of a volatile acid together in a high-shear mixer to produce the microparticles.

In particular embodiments, the method for making FDKP microparticles having a surface area ranging from about 35 $m^2/g$ to about 67 $m^2/g$ comprises a saponification reaction and a recrystallization. In one embodiment, there is disclosed a method of making microparticles suitable for pulmonary administration as a dry powder comprising: a) synthesizing an FDKP compound or composition, b) dissolving the FDKP compound of step b) in a solution having a basic pH to form an FDKP solution; d) providing a solution of a volatile acid, and e) mixing the FDKP solution with the solution of a volatile acid together in a high-shear mixer to produce the microparticles. The method can further comprise determining the specific surface area of the particles subsequent to particle formation.

In specific embodiments, the method of synthesizing FDKP microparticles having a specific surface area of less than about 67 $m^2/g$ comprises: feeding equal masses of about 10.5 wt % acetic acid and about 2.5 wt % FDKP solution at about 14° C. to about 18° C. through a high shear mixer, such as a Dual-feed SONOLATOR™ at 2000 psi through a 0.001-$in^2$ orifice to form a suspension. The method can further comprise the step of precipitating the microparticles out of solution and collecting the microparticles formed in a deionized water reservoir of about equal mass and temperature. In this embodiment, the suspension comprises a microparticle content of about 0.8% solids. In certain embodiments, the method further comprises concentrating the microparticle suspension by washing the microparticles in, for example, deionized water using a tangential flow filtration technique. In this and other embodiments, the precipitate can be first concentrated to about 4% solids then further washed with deionized water. In some embodiments, the suspension typically can be concentrated to about 10% solids based on the initial mass of FDKP composition used. The concentrated suspension can be assayed for solids content by an oven drying method. In embodiments disclosed herein, the method further comprises determining the surface area of the particles after the particles are dried.

In specific embodiments of the compositions and methods herein disclosed, the diketopiperazine microparticles having the specific surface area of less than about 67 $m^2/g$ utilizes a diketopiperazine having the formula 2,5-diketo-3,6-bis (N—X-4-aminobutyl) piperazine, wherein X is selected from the group consisting of fumaryl, succinyl, maleyl, and glutaryl. In an exemplary embodiment, the diketopiperazine has the formula 3,6-bis(N-fumaryl-4-aminobutyl)-2,5-diketopiperazine or 2,5-diketo-3,6-bis(N-fumaryl-4-amino-butyl) piperazine.

Another embodiment disclosed herein includes a method for making FDKP microparticles having a specific surface area of less than about 67 $m^2/g$ and comprising a drug or active agent, wherein the stated specific surface area is determined prior to addition of drug to the particle. In this embodiment, the method comprises adding a solution comprising the active agent, such as a peptide including insulin, glucagon, glucagon-like peptide-1, oxyntomodulin, peptide YY, and the like to the microparticle suspension; adding aqueous ammonia to the suspension to, for example, raise the pH of the suspension to pH 4.5; incubating the reaction, and flash-freezing the resultant suspension in liquid nitrogen and lyophilizing pellets formed to produce a dry powder comprising the FDKP microparticles having a specific surface area of less than about 67 $m^2/g$. In an aspect of this embodiment the specific surface area of the microparticles after adsorption of the active agent onto the microparticle is less than about 62 $m^2/g$.

In one embodiment there is disclosed a method of delivering insulin to a patient in need thereof comprising administering a dry powder comprising diketopiperazine microparticles having a specific surface area of less than about 62 $m^2/g$ (67 $m^2/g$ based on the unloaded microparticle) to the deep lung by inhalation of the dry powder by the patient. In aspects of this embodiment, particular features of an inhaler system are specified.

Another embodiment disclosed herein includes a method of delivering a drug, for example insulin, to a patient in need thereof comprising administering a dry powder to the deep lung by inhalation of the dry powder by the patient; wherein the dry powder comprises diketopiperazine microparticles comprising insulin; wherein the microparticles are formed of a diketopiperazine and have a surface area ranging from about 35 $m^2/g$ to about 67 $m^2/g$. In an aspect of this embodiment, the specific surface area of the microparticles after adsorption of the active agent onto the microparticle is less than about 62 $m^2/g$. In aspects of this embodiment, particular features of an inhaler system are specified. Further embodiments involve methods of treating an insulin-related disorder comprising administering a dry powder described above to a person in need thereof. In various embodiments an insulin-related disorder can specifically include or exclude any or all of pre-diabetes, type 1 diabetes mellitus (honeymoon phase, post-honeymoon phase, or both), type 2 diabetes mellitus, gestational diabetes, hypoglycemia, hyperglycemia, insulin resistance, secretory dysfunction, impaired early-phase release of insulin, loss of pancreatic β-cell function, loss of pancreatic β-cells, and metabolic disorder.

In one embodiment, a method of treating an endocrine-related disease or disorder comprising administering to a person in need thereof a dry powder formulation comprising FDKP microparticles having a specific surface area of less than about 67 $m^2/g$ and a drug suitable to treat said disease or disorder. In an aspect of this embodiment, the specific surface area of the microparticles after adsorption of the active agent onto the microparticle is less than about 62 $m^2/g$. One embodiment includes a method of treating an insulin-related disorder comprising administering a dry powder comprising microparticles of FDKP described above to a person in need thereof. The method comprises administering to a subject a dry powder formulation comprising microparticles of FDKP having a specific surface area of less than about 67 $m^2/g$ and insulin. In an aspect of this embodiment, the specific surface area of the microparticles after adsorption of the active agent onto the microparticle is less than about 62 $m^2/g$. In various embodiments, an insulin-related disorder can specifically include or exclude any or all of pre-diabetes, type 1 diabetes mellitus (honeymoon phase, post-honeymoon phase, or both), type 2 diabetes mellitus, gestational diabetes, hypoglycemia, hyperglycemia, insulin resistance, secretory dysfunction, impaired early-phase release of insulin, loss of pancreatic β-cell function, loss of pancreatic β-cells, and metabolic disorder. In one embodiment, the dry powder comprises insulin. In other embodiments, the dry powder comprises glucagon, an exendin, or GLP-1.

BRIEF DESCRIPTION OF THE DRAWINGS

The following drawings form part of the present specification and are included to further demonstrate certain aspects of the examples disclosed herein. The disclosure may be better understood by reference to one or more of these drawings in combination with the detailed description of specific embodiments presented herein.

FIG. 3 provides a schematic representation of a FDKP manufacturing process.

DETAILED DESCRIPTION

Figure 1A:
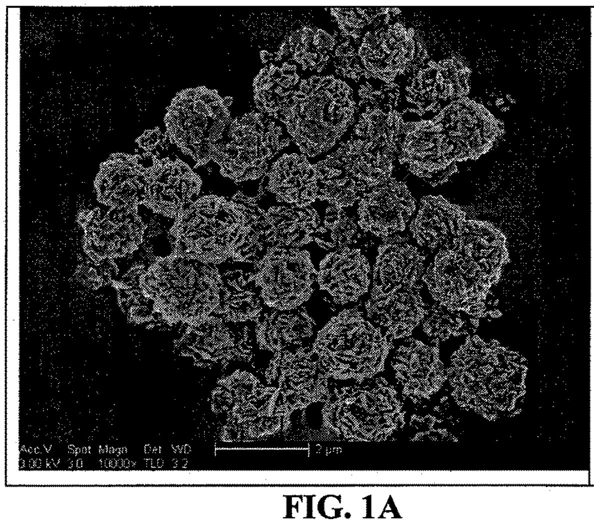
FIGS. 1A and 1B depict microparticles with high and low specific surface area (SSA) respectively.

As stated, drug delivery to the lungs offers many advantages. It is difficult to deliver drugs into the lungs, however, due to problems in transporting the drugs past natural physical barriers in a uniform volume and weight of the drug. Disclosed herein are diketopiperazines microparticles having a specific surface area of less than about 67 $m^2/g$ as drug delivery agents, methods of making the microparticles and methods of treatment using the microparticles.

As used herein, the term "microparticle" refers to a particle with a diameter of about 0.5 μm to about 1000 μm, irrespective of the precise exterior or interior structure. Microparticles having a diameter of between about 0.5 μm and about 10 μm can reach the lungs, successfully passing most of the natural barriers. A diameter of less than about 10 μm is required to navigate the turn of the throat and a diameter of about 0.5 μm or greater is required to avoid being exhaled. To reach the deep lung (or alveolar region) where most efficient absorption is believed to occur, it is preferred to maximize the proportion of particles contained in the "respirable fraction" (RF), generally accepted to be those particles with an aerodynamic diameter of about 0.5 μm to about 5.7 μm, though some references use somewhat different ranges, as measured using standard techniques, for example, with an Andersen Cascade Impactor. Other impactors can be used to measure aerodynamic particle size such as the NEXT GENERATION IMPACTOR™ (NGI™, MSP Corporation), for which the respirable fraction is defined by similar aerodynamic size, for example <6.4 μm. In some embodiments, a laser diffraction apparatus is used to determine particle size, for example, the laser diffraction apparatus disclosed in U.S. patent application Ser. No. 12/727,179, filed on Mar. 18, 2010, which is incorporated herein in its entirety for its relevant teachings, wherein the volumetric median geometric diameter (VMGD) of the particles is measured to assess performance of the inhalation system. For example, in various embodiments cartridge emptying of ≥80%, 85%, or 90% and a VMGD of the emitted particles of ≤12.5 μm, ≤7.0 μm, or ≤4.8 μm can indicate progressively better aerodynamic performance. Embodiments disclosed herein show that FDKP microparticles having a specific surface area of less than about 67 $m^2/g$ exhibit characteristics beneficial to delivery of drugs to the lungs such as improved aerodynamic performance.

Respirable fraction on fill (RF/fill) represents the percentage of particles from the filled dose that are emitted with sizes suitable for pulmonary delivery, which is a measure of microparticle aerodynamic performance. As described herein, a RF/fill value of 40% or greater than 40% reflects acceptable aerodynamic performance characteristics. In certain embodiments disclosed herein, the respirable fraction on fill can be greater than 50%. In an exemplary embodiment, a respirable fraction on fill can be up to about 80%, wherein about 80% of the fill is emitted with particle sizes <5.8 μm as measured using standard techniques.

As used herein, the term "dry powder" refers to a fine particulate composition that is not suspended or dissolved in a propellant, carrier, or other liquid. It is not meant to necessarily imply a complete absence of all water molecules.

It should be understood that specific RF/fill values can depend on the inhaler used to deliver the powder. Powders generally tend to agglomerate and crystalline DKP microparticles form particularly cohesive powders. One of the functions of a dry powder inhaler is to deagglomerate the powder so that the resultant particles comprise a respirable fraction suitable for delivering a dose by inhalation. However, deagglomeration of cohesive powders is typically incomplete so that the particle size distribution seen when measuring the respirable fraction as delivered by an inhaler will not match the size distribution of the primary particles, that is, the profile will be shifted toward larger particles. Inhaler designs vary in their efficiency of deagglomeration and thus the absolute value of RF/fill observed using different designs will also vary. However, optimal RF/fill as a function of specific surface area will be similar from inhaler to inhaler.

As used herein, the term "about" is used to indicate that a value includes the standard deviation of the measurement for the device or method being employed to determine the value.

Diketopiperazines

One class of drug delivery agents that has been used to overcome problems in the pharmaceutical arts such as drug instability and/or poor absorption are the 2,5-diketopiperazines. 2,5-Diketopiperazines are represented by the compound of the general Formula 1 as shown below wherein $E_1$ and $E_2$ are independently N or more particularly NH. In other embodiments, $E_1$ and/or $E_2$ are independently an oxygen or a nitrogen so that wherein either one of the substituents for $E_1$ and $E_2$ is an oxygen and the other is a nitrogen the formula yields the substitution analog diketomorpholine, or when both $E_1$ and $E_2$ are oxygen the formula yields the substitution analog diketodioxane.

Formula 1

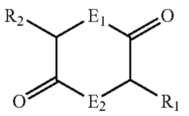

These 2,5 diketopiperazines have been shown to be useful in drug delivery, particularly those bearing acidic $R_1$ and $R_2$ groups as described in, for example, U.S. Pat. No. 5,352,461 entitled "Self Assembling Diketopiperazine Drug Delivery System;" U.S. Pat. No. 5,503,852 entitled "Method For Making Self-Assembling Diketopiperazine Drug Delivery System;" U.S. Pat. No. 6,071,497 entitled "Microparticles For Lung Delivery Comprising Diketopiperazine;" and U.S. Pat. No. 6,331,318 entitled "Carbon-Substituted Diketopiperazine Delivery System," each of which is incorporated herein by reference in its entirety for all that it teaches regarding diketopiperazines and diketopiperazine-mediated drug delivery. Diketopiperazines can be formed into microparticles that incorporate a drug or microparticles onto which a drug can be adsorbed. The combination of a drug and a diketopiperazine can impart improved drug stability and/or absorption characteristics. These microparticles can be administered by various routes of administration. As dry powders these microparticles can be delivered by inhalation to specific areas of the respiratory system, including the lungs.

Such microparticles are typically obtained by pH-based precipitation of the free acid (or base) resulting in self-assembled microparticles comprised of aggregated crystalline plates. The stability of the particle can be enhanced by small amounts of a surfactant, such as polysorbate-80, in the DKP solution from which the particles are precipitated (see for example US Patent Publication No. 2007/0059373 entitled "Method of drug formulation based on increasing the affinity of crystalline microparticle surfaces for active agents" which is incorporated herein by reference in its entirety for all that it teaches regarding the formation and loading of DKP microparticles and dry powders thereof). Ultimately solvent can be removed to obtain a dry powder. Appropriate methods of solvent removal include lyophilization and spray drying (see for example US Patent Publication No. 2007/0196503 entitled "A method for improving the pharmaceutic properties of microparticles comprising diketopiperazine and an active agent" and U.S. Pat. No. 6,444,226 entitled "Purification and stabilization of peptide and protein pharmaceutical agents" each of which is incorporated herein by reference in its entirety for all that it teaches regarding the formation and loading of DKP microparticles and dry powders thereof). The microparticles disclosed herein are distinct from microparticles composed of DKP salts. Such particles are typically formed (as opposed to dried) by spray drying, resulting in spheres and/or collapsed spheres of an amorphous salt (as opposed to a free acid or base) so that they are chemically, physically, and morphologically distinct entities. The present disclosure refers to FDKP to be understood as the free acid or the dissolved anion.

Methods for synthesizing diketopiperazines are described in, for example, Katchalski, et al., J. Amer. Chem. Soc. 68, 879-880 (1946) and Kopple, et al., J. Org. Chem. 33(2), 862-864 (1968), the teachings of which are incorporated herein by reference in their entirety. 2,5-Diketo-3,6-di(aminobutyl)piperazine (Katchalski et al. refer to this as lysine anhydride) can also be prepared via cyclodimerization of N-ε-P-L-lysine in molten phenol, similar to the Kopple method, followed by removal of the blocking (P)-groups with an appropriate reagent and conditions. For example, CBz-protecting groups can be removed using 4.3 M HBr in acetic acid. This route can be preferred because it uses a commercially available starting material, it involves reaction conditions that are reported to preserve stereochemistry of the starting materials in the product and all steps can be easily scaled up for manufacture. Methods for synthesizing diketopiperazines are also described in U.S. Pat. No. 7,709, 639, entitled, "Catalysis of Diketopiperazine Synthesis," which is also incorporated by reference herein for its teachings regarding the same.

Fumaryl diketopiperazine (3,6-bis(N-fumaryl-4-aminobutyl)-2,5-diketopiperazine; FDKP) is one preferred diketopiperazine for pulmonary applications:

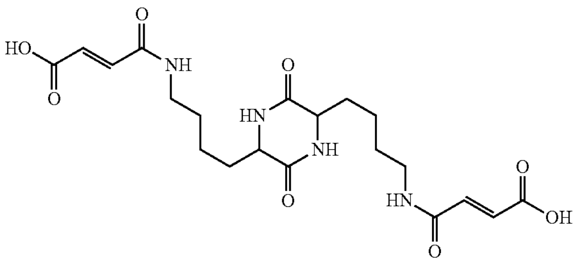 [SMILES: O=C(O)/C=C/C(=O)NCCCCC1NC(=O)C(CCCCNC(=O)/C=C/C(=O)O)NC1=O]

FDKP provides a beneficial microparticle matrix because it has low solubility in acid but is readily soluble at neutral or basic pH. These properties allow FDKP to crystallize and the crystals to self-assemble into microparticles under acidic conditions. The particles dissolve readily under physiological conditions where the pH is neutral. As noted, microparticles having a diameter of between about 0.5 and about 10 microns can reach the lungs, successfully passing most of the natural barriers. Particles in this size range can be readily prepared from FDKP.

As noted, microparticles having a diameter of between about 0.5 and about 10 microns can reach the lungs, successfully passing most of the natural barriers. Particles in this size range can be readily prepared from diketopiperazines with acidic groups, such as the carboxylate groups in FDKP (as well as in related molecules such as 2,5-diketo-3,6-di(4-X-aminobutyl)piperazine wherein X is succinyl, glutaryl, or maleyl). Upon acid precipitation self-assembled particles composed of aggregates of crystalline plates are obtained. The size of these plates relates to the specific surface area of the particles which in turn is implicated in effects on the structure, loading capacity, and aerodynamic performance of the particles.

The specific surface area of DKP microparticles is a measure of average crystal size and can be used to gauge the relative contributions of crystal nucleation and growth to microparticle characteristics. Specific surface area depends on the size of microparticle crystals and the density (ρ) of the microparticle matrix and is inversely proportional to the characteristic size, L, of the crystals. Specific surface area is a property of a population of particles and not necessarily a characteristic of each individual particle therein. Embodiments disclosed herein show that microparticles with a specific surface area less than about 67 $m^2/g$ exhibit characteristics beneficial to delivery of drugs to the lungs such as improved aerodynamic performance with moderately efficient inhalers such as the MEDTONE® inhaler disclosed in U.S. Pat. No. 7,464,706 entitled, "Unit Dose Cartridge and Dry Powder Inhaler," which is incorporated by reference herein for its teachings regarding the same. An alternate embodiment with a specific surface area less than about 62 $m^2/g$ provides a greater level of assurance that a batch of particles will meet a minimum aerodynamic performance standard. As specific surface area also affects drug loading/content capacity, various embodiments require specific surface areas greater than or equal to about 35 $m^2/g$, 40 $m^2/g$, or 45 $m^2/g$ for improved drug adsorption capacity. Additionally, as specific surface area falls below about 35 $m^2/g$ inconsistent cartridge emptying is observed even with high efficiency inhalers such as that disclosed in U.S. patent application Ser. No. 12/484,125, entitled, "A Dry Powder Inhaler and System for Drug Delivery," filed on Jun. 12, 2009, and U.S. patent application Ser. No. 12/717,884, entitled, "Improved Dry Powder Drug Delivery System," filed on Mar. 4, 2010, which disclosures are herein incorporated by reference for its teachings regarding the same.

Upper Limit of the Specific Surface Area Range

The upper limit of the specific surface area range defined herein is compelled by the aerodynamic performance of the microparticles. Studies described herein have demonstrated that there is a tendency toward lower RF/fill values as specific surface area values increase above about 50 $m^2/g$. Additionally, as specific surface area increases, there is a broadening in the distribution of RF/fill, and an increasing probability of failing a chosen criterion of an RF/fill, for example RF/fill >40%. In some embodiments therefore an upper limit of about 67 $m^2/g$ can be chosen. Based on the curve fitted to collected data for a large number of preparations this value is predicted to provide an RF/fill of 40%. In other embodiments, an upper limit of about 62 $m^2/g$ can be chosen. The 62 $m^2/g$ upper limit provides microparticles with acceptable RF/fill values within a 95% confidence limit (see FIG. 6A).

Another reason to impose an upper limit on the specific surface area of microparticles is that suspensions of microparticles with high specific surface area tend to be orders of magnitude more viscous than suspensions of microparticles with lower specific surface area. This phenomenon likely reflects the increase in inter-particle attraction associated with smaller crystals. Upon freeze drying, the stronger attraction may generate aggregates that are not effectively deagglomerated, potentially reducing RF/fill as suspension viscosity is negatively correlated with RF/fill.

Microparticle specific surface area is determined from lyophilized bulk powder and is not predicted exactly from microparticle formation conditions. Accordingly, it can be desirable to target a specific surface area of about 52 $m^2/g$. With about 52 $m^2/g$ set as a specific surface area target, only 5% of microparticles would be expected to exceed the more conservative upper limit of 62 $m^2/g$ (FIG. 6B). Within this 5% of the microparticles that may exceed 62 $m^2/g$, only a further 5% (0.25%) would be expected to exhibit an RF/fill of <40%. These manufacturing conditions would thus provide microparticles having an RF/fill of >40% with over a 99% confidence limit.

Lower Limit of the Specific Surface Area Range

Figure 1B:
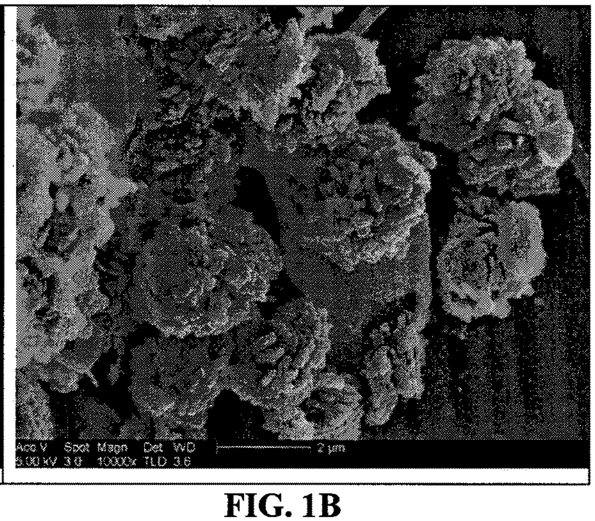

The lower limit of the specific surface area range defined herein is compelled by drug loading requirements. Microparticles must have a specific surface area that is sufficient to load required drug amounts. If drug is not sufficiently adsorbed (i.e., is left in solution), the non-adsorbed drug can "bridge" the formed microparticles leading to the formation of aggregates. Aggregates can adversely affect aerodynamic characteristics. In the case of insulin, to avoid bridging by insulin at an appropriate therapeutic dose, a lower specific surface area limit of about 35 $m^2/g$ is required. Bridging is also a possible cause for the poor cartridge emptying, noted above, that can occur with powders with lower specific surface area. To provide greater assurance that these problems can be avoided and that loading can be maximized, still higher lower limits on specific surface area, for example 40 or 45 $m^2/g$ can be used. Alternatively, other factors impacting aerodynamic performance can be maintained within more narrow tolerances. FIG. 1A shows a cluster of microparticles with a high specific surface area. FIG. 1B shows the "bridging" of particles by insulin in a powder with a low specific surface area.

FDKP Microparticle Formation.

Figure 2:
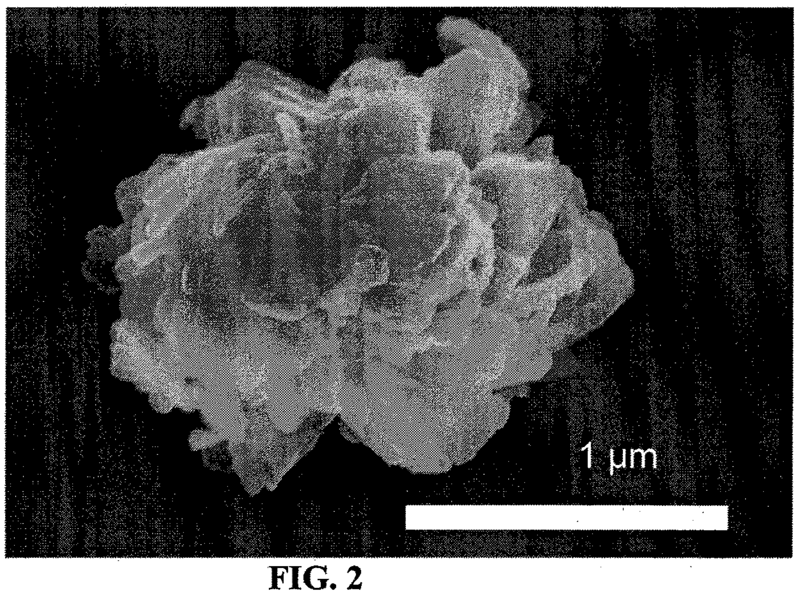
FIG. 2 depicts an fumaryl diketopiperazine (FDKP) microparticle having an overall spherical morphology.
Figure 4A:
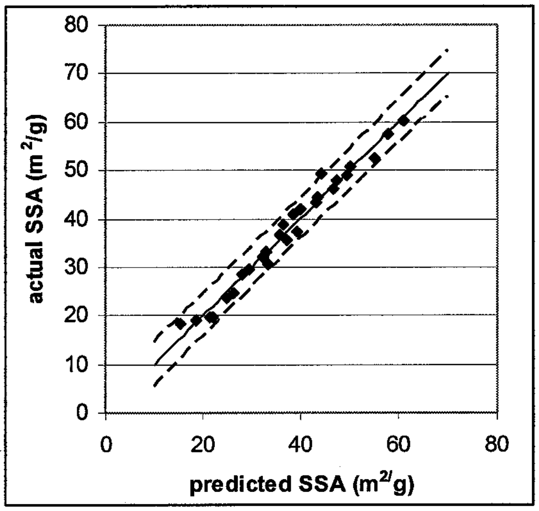
FIGS. 4A and 4B depict the estimated and actual SSA of microparticle/insulin powders manufactured according to the schematic shown in FIG. 3.
Figure 4B:
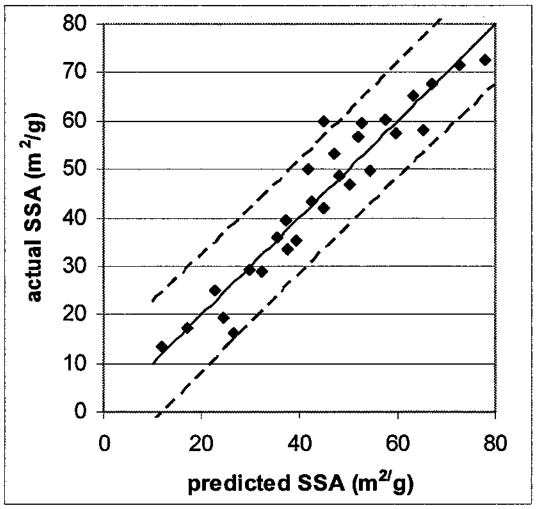

The first step in the manufacture of FDKP microparticles is the formation of the microparticles by pH-induced crystallization of FDKP and the self-assembly of the FDKP crystals into microparticles having an overall spherical morphology (FIG. 2). Accordingly, the manufacture of microparticles is essentially a crystallization process. Excess solvent can be removed by washing the suspension by repeated centrifugation, decantation and re-suspension, or by diafiltration.

To form insulin-loaded FDKP microparticles, insulin can be adsorbed directly onto the microparticles while in suspension (i.e. prior to freeze drying) by adding an insulin stock solution to the FDKP microparticle suspension. In one embodiment, a pH control step can also be performed after the addition of the insulin stock solution. This step can promote insulin adsorption onto the microparticles in suspension prior to further processing. Increasing the pH of the suspension to about 4.5 promotes complete insulin adsorption onto the microparticles in suspension without excessive dissolution of the FDKP from the particle matrix and also improves the stability of insulin in the bulk drug product. The suspension can be flash-frozen drop-wise (i.e. cryo-pelletized) in liquid nitrogen and lyophilized to remove the solvent and obtain a dry powder. In alternative embodiments the suspension can be spray-dried to obtain the dry powder. FIG. 3 provides a schematic representation of an appropriate manufacturing process.

In one embodiment, a manufacturing process for making the present FDKP microparticles containing insulin is provided. In summary, using a high shear mixer such as a Dual-feed SONOLATOR™, or for example, the high shear mixer as disclosed in U.S. Provisional Patent Application Ser. No. 61/257,311, filed on Nov. 2, 2009, which disclosures are incorporated herein by reference in their entirety, equal masses of about 10.5 wt % acetic acid and about 2.5 wt % FDKP solutions at about 16° C.±about 2° C. (Tables 1 and 2) can be fed at 2000 psi by a Dual-feed SONOLATOR™ through a 0.001-$in^2$ orifice. The precipitate can be collected in a deionized (DI) water reservoir of about equal mass and temperature. The resultant suspension comprises about 0.8% solids. The precipitate can be concentrated and washed by tangential flow filtration. The precipitate can be first concentrated to about 4% solids then washed with deionized water. The suspension can be finally concentrated to about 10% solids based on the initial mass of FDKP. The concentrated suspension can be assayed for solids content by an oven drying method.

In one embodiment, a concentrated insulin stock solution can be prepared with 1 part insulin and 9 parts about 2 wt % acetic acid. The insulin stock can be added gravimetrically to the suspension to obtain a load of about 11.4 wt % insulin. The insulin-FDKP suspension can be mixed at least about 15 minutes. In some embodiments, mixing can take a shorter or longer time. The insulin-FDKP suspension can then be titrated with about 14 to about 15 wt % aqueous ammonia to a pH of about 4.5 from an initial pH of about 3.5. The suspension can be flash-frozen in liquid nitrogen to form pellets and lyophilized to yield the bulk insulin-containing FDKP microparticles. Blank FDKP microparticles can be manufactured identically minus the insulin loading and pH adjustment steps. In one embodiment, the density of the FDKP-insulin bulk powder comprising the microparticles described herein is from about 0.2 $g/cm^3$ to about 0.3 $g/cm^3$.

TABLE 1

10.5% Acetic Acid Solution

| Component | wt % |
|---|---|
| DI Water | 89.00 |
| Glacial acetic acid (GAA) | 10.50 |
| 10% Polysorbate 80 | 0.50 |

0.2 μm filtered

TABLE 2

2.5% FDKP Solution

| Component | wt % |
|---|---|
| DI Water | 95.40 |
| FDKP | 2.50 |
| $NH_4OH$ | 1.60 |
| 10% Polysorbate 80 | 0.50 |

0.2 μm filtered

Controlling Specific Surface Area

The size distribution and shape of FDKP crystals are affected by the balance between the nucleation of new crystals and the growth of existing crystals. Both phenomena depend strongly on concentrations and supersaturation in solution. The characteristic size of the FDKP crystal is an indication of the relative rates of nucleation and growth. When nucleation dominates, many crystals are formed but they are relatively small because they all compete for the FDKP in solution. When growth dominates, there are fewer competing crystals and the characteristic size of the crystals is larger.

Crystallization depends strongly on supersaturation which, in turn, depends strongly on the concentration of the components in the feed streams. Higher supersaturation is associated with the formation of many small crystals; lower supersaturation produces fewer, larger crystals. In terms of supersaturation: 1) increasing the FDKP concentration raises the supersaturation; 2) increasing the concentration of ammonia shifts the system to higher pH such as to about pH 4.5, raises the equilibrium solubility and decreases the supersaturation; and 3) increasing the acetic acid concentration increases the supersaturation by shifting the endpoint to lower pH where the equilibrium solubility is lower. Decreasing the concentrations of these components induces the opposite effects.

Temperature affects FDKP microparticle formation through its effect on FDKP solubility and the kinetics of FDKP crystal nucleation and growth. At low temperatures, small crystals are formed with high specific surface area. Suspensions of these particles exhibit high viscosity indicating strong inter-particle attractions. A temperature range of about 12° C. to about 26° C. provides RF/fill >40% at the 95% confidence level. By accounting for the relationship between temperature and specific surface area, a slightly narrower but internally consistent temperature range of about 13° C. to about 23° C. can be used.

Finally it should be realized that adsorption of an active agent onto the surfaces of the microparticles tends to reduce the specific surface area. Adsorption of the active agent may fill, or otherwise occlude, some of the narrower spaces between the crystalline plates that make up the particle, thereby reducing specific surface area. Additionally, the adsorption of an active agent adds mass to the microparticle without substantially affecting the diameter (size) of the microparticle. As specific surface area is inversely proportional to the mass of the microparticle a reduction in specific surface area will occur.

Selection and Incorporation of Active Agents

As long as the microparticles described herein retain the required specific surface area of less than about 67 $m^2/g$, they can adopt other additional characteristics beneficial for delivery to the lung and/or drug adsorption. U.S. Pat. No. 6,428,771 entitled "Method for Drug Delivery to the Pulmonary System" describes DKP particle delivery to the lung and is incorporated by reference herein for its teachings regarding the same. U.S. Pat. No. 6,444,226, entitled, "Purification and Stabilization of Peptide and Protein Pharmaceutical Agents" describes beneficial methods for adsorbing drugs onto microparticle surfaces and is also incorporated by reference herein for its teachings regarding the same. Microparticle surface properties can be manipulated to achieve desired characteristics as described in U.S. patent application Ser. No. 11/532,063 entitled "Method of Drug Formulation based on Increasing the Affinity of Crystalline Microparticle Surfaces for Active Agents" which is incorporated by reference herein for its teachings regarding the same. U.S. patent application Ser. No. 11/532,065 entitled "Method of Drug Formation based on Increasing the Affinity of Active Agents for Crystalline Microparticle Surfaces" describes methods for promoting adsorption of active agents onto microparticles. U.S. patent application Ser. No. 11/532,065 is also incorporated by reference herein for its teachings regarding the same.

The microparticles described herein can comprise one or more active agents. As used herein "active agent", used interchangeably with "drug", refers to pharmaceutical substances, including small molecule pharmaceuticals, biologicals and bioactive agents. Active agents can be naturally occurring, recombinant or of synthetic origin, including proteins, polypeptides, peptides, nucleic acids, organic macromolecules, synthetic organic compounds, polysaccharides and other sugars, fatty acids, and lipids, and antibodies and fragments thereof, including, but not limited to, humanized or chimeric antibodies, F(ab), $F(ab)_2$, a single-chain antibody alone or fused to other polypeptides or therapeutic or diagnostic monoclonal antibodies to cancer antigens. The active agents can fall under a variety of biological activity and classes, such as vasoactive agents, neuroactive agents, hormones, anticoagulants, immunomodulating agents, cytotoxic agents, antibiotics, antiviral agents, antigens, infectious agents, inflammatory mediators, hormones, and cell surface antigens. More particularly, active agents can include, in a non-limiting manner, cytokines, lipokines, enkephalins, alkynes, cyclosporins, anti-IL-8 antibodies, IL-8 antagonists including ABX-IL-8; prostaglandins including PG-12, LTB receptor blockers including LY29311, BIIL 284 and CP105696; triptans such as sumatriptan and palmitoleate, insulin and analogs thereof, growth hormone and analogs thereof, parathyroid hormone (PTH) and analogs thereof, parathyroid hormone related peptide (PTHrP), ghrelin, obestatin, enterostatin, granulocyte macrophage colony stimulating factor (GM-CSF), amylin, amylin analogs, glucagon-like peptide 1 (GLP-1), clopidogrel, PPACK (D-phenylalanyl-L-prolyl-L-arginine chloromethyl ketone), oxyntomodulin (OXM), peptide YY(3-36) (PYY), adiponectin, cholecystokinin (CCK), secretin, gastrin, glucagon, motilin, somatostatin, brain natriuretic peptide (BNP), atrial natriuretic peptide (ANP), IGF-1, growth hormone releasing factor (GHRF), integrin beta-4 precursor (ITB4) receptor antagonist, nociceptin, nocistatin, orphanin FQ2, calcitonin, CGRP, angiotensin, substance P, neurokinin A, pancreatic polypeptide, neuropeptide Y, delta-sleep-inducing peptide and vasoactive intestinal peptide. The microparticles can also be used to deliver other agents, for example, contrast dyes such as Texas Red.

The drug content to be delivered on microparticles formed from FDKP having a specific surface area less than about 67 $m^2/g$ is typically greater than 0.01%. In one embodiment, the drug content to be delivered with the microparticles having the aforementioned specific surface area, can range from about 0.01% to about 20%, which is typical for peptides such as insulin. For example, if the drug is insulin, the present microparticles typically comprise 3-4 U/mg (approximately 10 to 15%) insulin. In certain embodiments, the drug content of the particles can vary depending on the form and size of the drug to be delivered.

As long as the microparticles described herein retain the required specific surface area, they can adopt other additional characteristics beneficial for delivery to the lung and/or drug adsorption. U.S. Pat. No. 6,428,771 entitled "Method for Drug Delivery to the Pulmonary System" describes DKP particle delivery to the lung and is incorporated by reference herein for its teachings regarding the same. U.S. Pat. No. 6,444,226, entitled, "Purification and Stabilization of Peptide and Protein Pharmaceutical Agents" describes beneficial methods for adsorbing drugs onto microparticle surfaces and is also incorporated by reference herein for its teachings regarding the same. Microparticle surface properties can be manipulated to achieve desired characteristics as described in U.S. patent application Ser. No. 11/532,063 entitled "Method of Drug Formulation based on Increasing the Affinity of Crystalline Microparticle Surfaces for Active Agents" which is incorporated by reference herein for its teachings regarding the same. U.S. patent application Ser. No. 11/532,065 entitled "Method of Drug Formation based on Increasing the Affinity of Active Agents for Crystalline Microparticle Surfaces" describes methods for promoting adsorption of active agents onto microparticles. U.S. patent application Ser. No. 11/532,065 is also incorporated by reference herein for its teachings regarding the same.

EXAMPLES

The following examples are included to demonstrate embodiments of the disclosed microparticles. It should be appreciated by those of skill in the art that the techniques disclosed in the examples which follow represent techniques discovered by the inventor to function well in the practice of the present disclosure, and thus can be considered to constitute preferred modes for its practice. However, those of ordinary skill in the art should, in light of the present disclosure, appreciate that many changes can be made in the specific embodiments which are disclosed and still obtain a like or similar result.

Example 1

I. Manufacturing Procedures

A. General Manufacturing Procedures for FDKP/Insulin Microparticle Production

Microparticles were manufactured from fumaryl diketopiperazine (FDKP) and insulin. FDKP was dissolved in aqueous $NH_4OH$ to form a solution. A feed stream of this solution was combined with a feed stream of an aqueous acetic acid (HOAc) solution in a high shear mixer to form an aqueous suspension of microparticles.

The FDKP feed solution was prepared with about 2.5 wt % FDKP, about 1.6 wt % concentrated $NH_4OH$ (about 28 to about 30 wt % $NH_3$) and about 0.05 wt % polysorbate 80. The acetic acid feed solution was prepared at about 10.5 wt % glacial acetic acid and about 0.05 wt % polysorbate 80. Both feed solutions were filtered through an about 0.2 μm membrane prior to use.

FIG. 3 depicts a schematic representation of a manufacturing process for making the present FDKP microparticles containing insulin. In this embodiment, using a high shear mixer, for example, Dual-Feed SONOLATOR™ or the one as disclosed in U.S. Provisional Patent Application Ser. No. 61/257,311, filed on Nov. 2, 2009, which disclosure is incorporated herein by reference in its entirety, equal amounts (by mass) of each feed solution were pumped through the Dual-Feed SONOLATOR™ equipped with the #5 orifice (0.0011 sq. inch). The minor pump was set to 50% for equal flow rates of each feed stream and the feed pressure was about 2000 psi. The receiving vessel contained DI water equal to the mass of either feed solution (e.g. 4 kg FDKP feed solution and 4 kg HOAc feed solution would be pumped through the SONOLATOR™ into the receiving vessel containing 4 kg of DI water).

The resulting suspension was concentrated and washed by means of tangential flow filtration using a 0.2 $m^2$ PES (polyethersulfone) membrane. The suspensions were first concentrated to about 4% solids then diafiltered with DI water and finally concentrated to about 16% nominal solids. The actual percent solids of the washed suspension was determined by "loss on drying." Alternative methods can be used to measure the percent solids in a suspension such as the one disclosed in U.S. Provisional Patent Application Ser. No. 61/332,292, filed on May 7, 2010, entitled, "Determining Percent Solids in Suspension Using Raman Spectroscopy," which disclosure is incorporated herein by reference for its teachings.

Insulin stock solutions were prepared containing about 10 wt % insulin (as received) in a solvent comprising about 2 wt % HOAc in DI water, and sterile filtered. Based on the solids content of the suspension, the appropriate amount of stock solution was added to the mixed suspension. The resulting microparticle/insulin suspension was then adjusted by regulating the pH of the suspension from a pH of about 3.6 to a pH of about 4.5 using an ammonia solution.

The suspension comprising FDKP microparticles containing insulin was transferred to a cryogranulator/pelletizer, for example, as disclosed in U.S. Provisional Patent Application Ser. No. 61/257,385, filed on Nov. 2, 2009, which disclosure is incorporated herein by reference in its entirety, and pelletized by flash freezing in liquid nitrogen. The ice pellets were lyophilized to produce a dry powder.

B. Manufacturing Procedures for FDKP/Insulin Microparticle Production Used in 5% and 10% Studies In the 5% and 10% studies, the effects of feed concentrations on specific surface area and powder aerodynamics were examined. In the 5% studies, the experiments were designed to determine the effects of three factors, i.e., concentrations of FDKP, ammonia and acetic acid and examined in a 3×3 factorial experiment, in which the high and low levels were 5% from control conditions. In the 10% studies, concentrations of FDKP, ammonia and acetic acid were also examined in a 3×3 factorial experiment, however, the high and low levels were 10% from control conditions.

TABLE 3

Microparticle Formation Conditions Evaluated

| Level | FDKP (wt % in feed solution) | Strong Ammonia Solution (wt % in feed solution) | Acetic Acid (HOAc) (wt % in feed solution) |
|---|---|---|---|
| +10% | 2.75 | 1.76 | 11.55 |
| +5% | 2.63 | 1.68 | 11.03 |
| Control | 2.50 | 1.60 | 10.50 |
| −5% | 2.38 | 1.52 | 9.98 |
| −10% | 2.25 | 1.44 | 9.45 |

Note:
All feed solutions contained about 0.05 wt % polysorbate 80 and were maintained at about 16° C. unless otherwise noted.

C. End Measures

The respirable fraction (RF/fill) of bulk powders is a measure of aerodynamic performance and microparticle size distribution and is determined by testing with the Andersen cascade impactor. To obtain RF/fill values, cartridges are filled with bulk powder and discharged through a MEDTONE® inhaler at about 30 L/min. The powder collected on each inhaler stage is weighed and the total powder collected is normalized to the total amount filled in the cartridges. Accordingly, RF/fill is powder collected on those stages of the impactor representing the respirable fraction divided by powder loaded into cartridges.

The specific surface area (SSA) of microparticles is determined by adsorption of nitrogen and reported in terms of BET (Brunauer-Emmett-Teller) surface area using specific surface area analyzer (MICROMERITICS® TriStar 3000 Surface Area and Porosity Analyzer). The specific surface area depends on the size of the crystals and the density (ρ) of the microparticle matrix and is inversely proportional to the characteristic size, L, of the FDKP crystals:

$$SSA = \frac{\text{surface area}}{\text{mass}} \sim \frac{L^2}{\rho L^3} \sim L^{-1}$$

II. Effect of Feed Conditions on Specific Surface Area

Specific surface area was measured on all powders prepared in the 5% and 10% studies. Specific surface area was predicted by linear regression equations (see FIG. 3). The standard deviations of the predictions were ±2 $m^2/g$ for the 5% study and ±5.6 $m^2/g$ for the 10% study. These results were in line with theoretical expectations: higher FDKP concentrations, higher HOAc concentrations or lower ammonia concentrations increased the specific surface area (produced smaller crystals) by promoting crystal nucleation.

III. Effect of Temperature

The effect of temperature on particle properties was investigated in a series of studies in which the feed solution characteristics except for temperature were set at control conditions. Feed solution temperatures ranged from 4-32° C. The specific surface area of the microparticle powders and the RF/fill of the resulting microparticle powders were both determined.

Figure 5A:
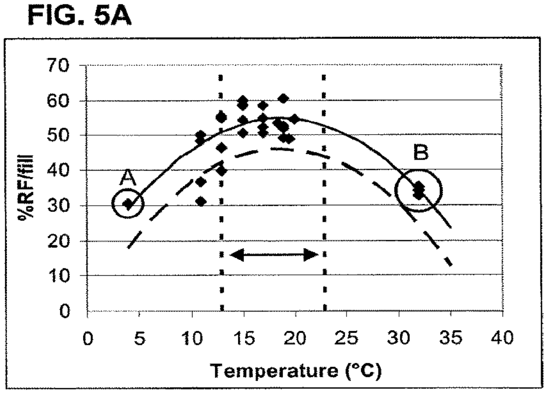
FIGS. 5A-C depict the relationships among RF/fill, SSA (of FDKP microparticles) and feed solution temperature.
Figure 5B:
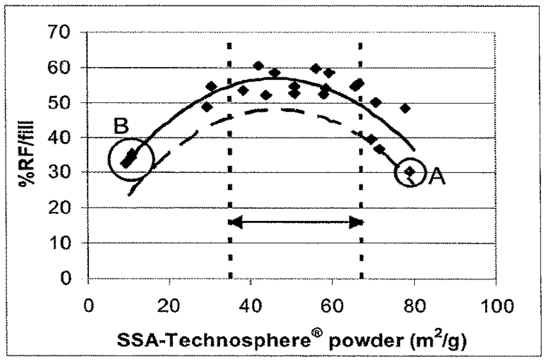
Figure 5C:
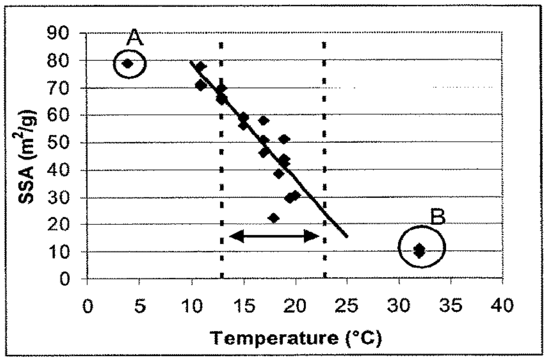

RF/fill, specific surface area and temperature were cross-plotted in FIG. 5. (RF/fill is determined with the insulin containing microparticles; the specific surface areas plotted are those determined for the particles prior to adsorption of insulin). The RF/fill of the microparticle powders was maximized near about 18° C. to about 19° C. (FIG. 5A). The dashed curve is the one-sided 95% lower confidence limit of the prediction (i.e., values above the curve are expected with 95% probability). A temperature range of about 12° C. to about 26° C. would provide RF/fill >40% at the 95% confidence level. When RF/fill is plotted against specific surface area of blank (drug-free) microparticle powders (FIG. 5B), the resulting curve resembles that for temperature. However, the order of the points is reversed. (For example, sample, "A," now appears at the right end of the axis while the samples "B" are at the left.) Microparticles with a specific surface area of 26-67 $m^2/g$ provides RF/fill >40% at the 95% confidence level. By accounting for the relationship between temperature and specific surface area (FIG. 5C), a slightly narrower but internally consistent temperature range of about 13° C. to about 23° C. was identified for particle formation.

IV. Effects of Specific Surface Area on RF/Fill

Figure 6A:
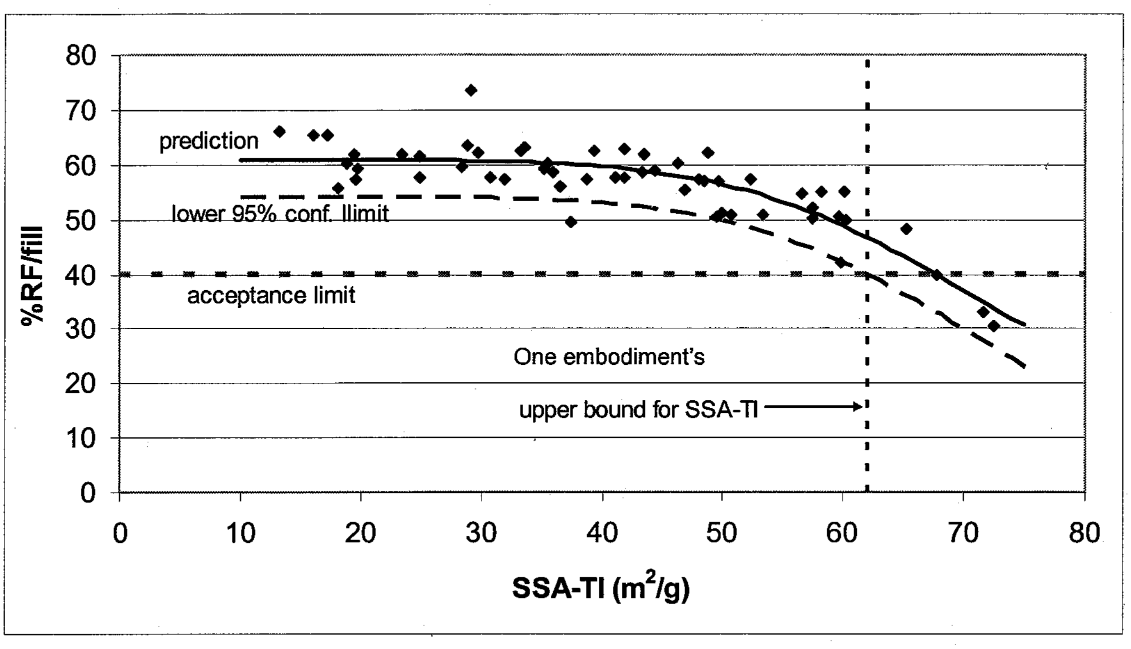
FIG. 6A depicts the relationship between RF/fill and the SSA of microparticle/insulin powders and shows that powders with an SSA >about 62 $m^2/g$ have a 5% probability of an RF/fill <40%.
Figure 6B:
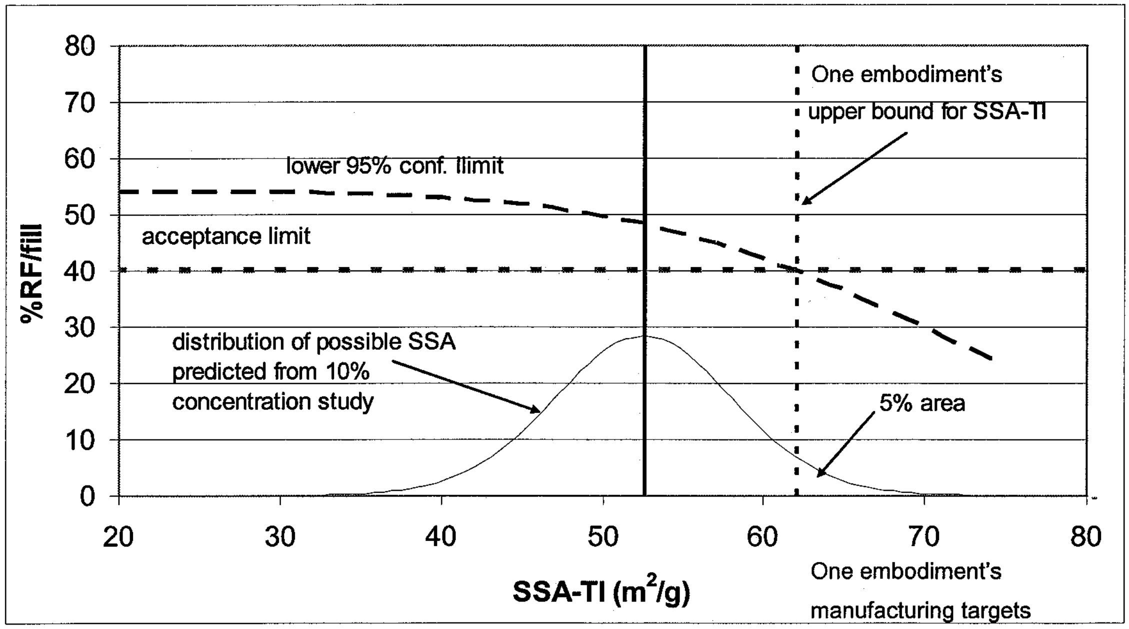
FIG. 6B shows a manufacturing target for SSA due to the uncertainty in predicting SSA from feed concentrations.

There is a tendency towards lower RF/fill values at specific surface area values above about 50 $m^2/g$ (FIG. 6A). An upper limit of about 62 $mg^2/g$ can be used while still maintaining a 95% confidence limit in appropriate RF/fill values (that is >40%; FIG. 6B).

Figure 7:
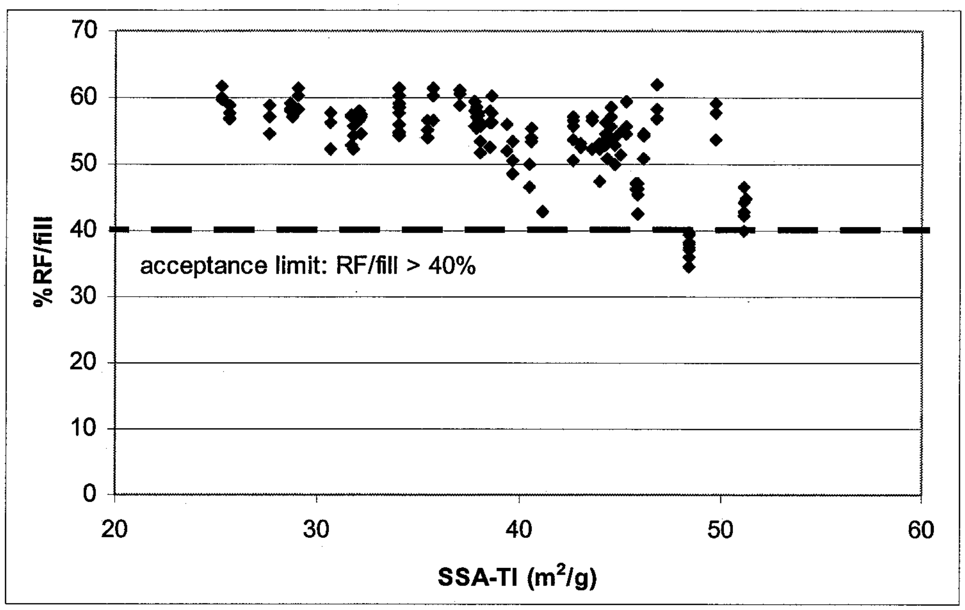
FIG. 7 depicts RF/fill as a function of SSA of microparticle/insulin powders. Each point represents a different batch of microparticle/insulin powders.
Figure 8A:
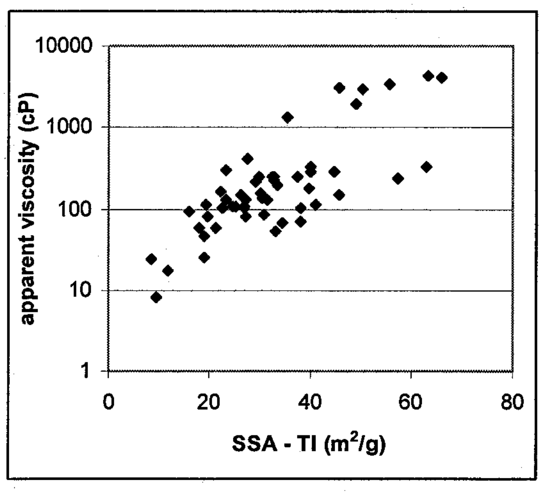
FIG. 8A depicts the effect of SSA of microparticle/insulin powders on the apparent viscosity of a microparticle suspension at about 4% solids.
Figure 8B:
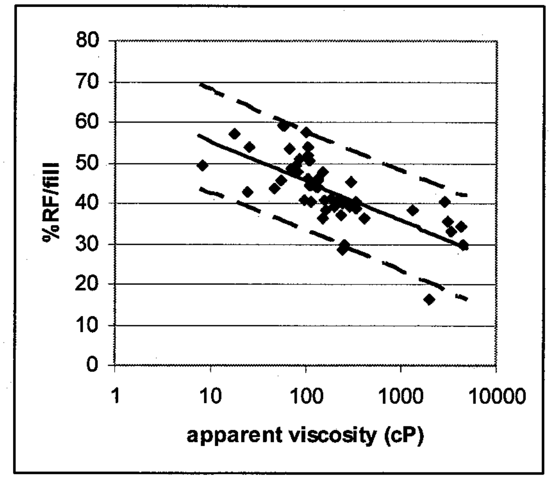
FIG. 8B depicts the relationship between suspension viscosity and powder performance.

FIG. 7 shows that as specific surface area increases at the upper range, there is a broadening in the distribution of RF/fill, and a higher probability of failing the chosen criterion of RF/fill >40%. FIG. 8*a* shows that suspensions of microparticles with high specific surface area for example, about 67 $m^2/g$ tend to be orders of magnitude more viscous as measured by a Brookfield Viscometer (Brookfield Engineering Laboratories, Inc., Middleboro, Mass.) than suspensions of microparticles with lower specific surface area, for example, about <14 $m^2/g$. FIG. 8B shows that suspension viscosity is negatively correlated with RF/fill.

V. Specific Surface Area and Insulin Adsorption

The relationship between specific surface area and insulin adsorption was investigated.

Suspensions of microparticles were prepared as described previously for the 5% and 10% study batches and loaded at about 11.4% insulin. Additionally, microparticles formed with control feed concentrations but feed solution temperatures ranging from about 4° C. to about 32° C. were also evaluated. Titrated suspensions had the pH of the suspension raised from about pH 3.6 to about pH 4.5 by serial addition of single drops of 14 wt % ammonia. Samples of the titrated suspension and supernatant were assayed for insulin concentration. All suspensions (titrated and untitrated) were lyophilized to produce dry powders. Powders were tested for specific surface area using a MICROMERITICS® TriStar 3000.

Figure 9:
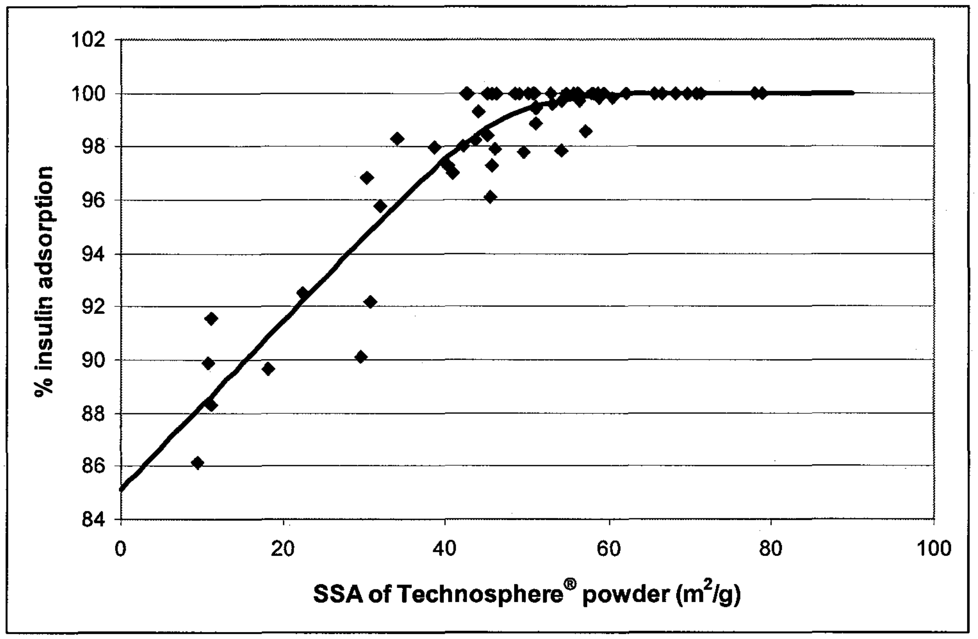
FIG. 9 depicts insulin concentration in supernatant as a function of SSA of FDKP microparticles.

At low specific surface area, there is a linear relationship between the amount of unbound insulin and specific surface area (FIG. 9). Adsorption of at least 95% of the insulin occurs when specific surface area is greater than about 35 $m^2/g$. The extent of insulin adsorption continues to increases with specific surface area up to about 40 $m^2/g$. Above this specific surface area, the microparticles adsorbed almost all of the insulin.

The results of these studies suggest beneficial lower and upper limits for microparticle specific surface area of about 35 $m^2/g$ to about 62 $m^2/g$. Providing microparticles in which greater than 80%, or greater than 90%, or greater than 95%, of microparticles have specific surface areas in this range provides microparticles with beneficial RF/fill and drug adsorption characteristics within a 95% confidence limit.

Example 2

Geometric Particle Size Analysis of Emitted Formulations by Volumetric Median Geometric Diameter (VMGD) Characterization Laser diffraction of dry powder formulations emitted from dry powder inhalers is a common methodology employed to characterize the level of deagglomeration subjected to a powder. The methodology indicates a measure of geometric size rather than aerodynamic size as occurring in industry standard impaction methodologies. Typically, the geometric size of the emitted powder includes a volumetric distribution characterized by the median particle size, VMGD. Importantly, geometric sizes of the emitted particles are discerned with heightened resolution as compared to the aerodynamic sizes provided by impaction methods. Smaller sizes are preferred and result in greater likelihood of individual particles being delivered to the pulmonary tract. Thus, differences in inhaler deagglomeration and ultimate performance can be easier to resolve with diffraction. In these experiments, inhalers were tested with laser diffraction at pressures analogous to actual patient inspiratory capacities to determine the effectiveness of the inhalation system to deagglomerate powder formulations. Specifically, the formulations included cohesive diketopiperazine powders with an active insulin loaded ingredient and without. These powder formulations possessed characteristic surface areas, isomer ratios, and Carr's indices. Reported in Table 4 are a VMGD and an efficiency of the container emptying during the testing. FDKP powders have an approximate Carr's index of 50 and TI powder has an approximate Carr's index of 40.

TABLE 4

| Inhaler system | powder | % trans | SSA | pressure drop (kPa) | sample size | % CE | VMGD (micron) |
|---|---|---|---|---|---|---|---|
| DPI 2 | FDKP | 56 | 55 | 4 | 15 | 92.5 | 6.800 |
| MEDTONE ® | FDKP | 56 | 55 | 4 | 30 | 89.5 | 21.200 |
| DPI 2 | FDKP + active | 56 | 45 | 4 | 30 | 98.0 | 4.020 |
| DPI 2 | FDKP + active | 56 | 45 | 4 | 20 | 97.0 | 3.700 |
| DPI 2 | FDKP + active | 56 | 45 | 4 | 20 | 98.4 | 3.935 |
| DPI 2 | FDKP + active | 56 | 45 | 4 | 20 | 97.8 | 4.400 |
| MEDTONE ® | FDKP + active | 56 | 45 | 4 | 10 | 86.1 | 9.280 |
| MEDTONE ® | FDKP + active | 56 | 45 | 4 | 10 | 92.3 | 10.676 |
| DPI 2 | FDKP + active | 56 | 45 | 2 | 7 | 92.9 | 4.364 |
| DPI 2 | FDKP + active | 56 | 45 | 2 | 7 | 95.1 | 4.680 |
| DPI 2 | FDKP + active | 56 | 45 | 4 | 7 | 97.0 | 3.973 |
| DPI 2 | FDKP + active | 56 | 45 | 4 | 7 | 95.5 | 4.250 |
| DPI 2 | FDKP + active | 56 | 56 | 4 | 10 | 99.6 | 6.254 |
| DPI 2 | FDKP + active | 56 | 14 | 4 | 10 | 85.5 | 4.037 |
| MEDTONE ® | FDKP + active | 56 | 56 | 4 | 20 | 89.7 | 12.045 |
| MEDTONE ® | FDKP + active | 56 | 14 | 4 | 20 | 37.9 | 10.776 |
| DPI 2 | FDKP + active | 54 | 50 | 4 | 10 | 97.1 | 4.417 |
| DPI 2 | FDKP + active | 54 | 44 | 4 | 10 | 96.0 | 4.189 |
| DPI 2 | FDKP + active | 56 | 35 | 4 | 10 | 92.0 | 3.235 |
| DPI 2 | FDKP + active | 50 | 34 | 4 | 10 | 93.2 | 5.611 |
| DPI 2 | FDKP + active | 66 | 33 | 4 | 10 | 79.0 | 4.678 |
| DPI 2 | FDKP + active | 45 | 42 | 4 | 10 | 93.2 | 5.610 |
| DPI 2 | FDKP + active | 56 | 9 | 4 | 10 | 78.9 | 5.860 |

The data in Table 4 show an improvement in powder deagglomeration in inhalers identified as DPI 2 over the MEDTONE® inhaler system. Diketopiperazine formulations with surface areas ranging from 14-56 $m^2/g$ demonstrated emptying efficiencies in excess of 85% and VMGD less than 7 microns. Similarly, formulations possessing an isomer ratio ranging from 45-66% trans demonstrated improved performance over the predicate device. However, it is worth noting that even with the more efficient inhaler at <15 $m^2/g$ there was a reduction in cartridge emptying indicating a fall off (decrease) in aerodynamic performance as trans isomer content departs from the desired range disclosed herein. Lastly, performance of the inhaler system with formulations characterized with Carr's indices of 40-50 were shown to be improved over the predicate device as well. In all cases, the reported VMGD values were below 7 microns.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects those of ordinary skill in the art to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above cited references and printed publications are herein individually incorporated by reference in their entirety.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed:

1. A dry powder pharmaceutical composition comprising inhalable 3,6-di(N-fumaryl-4-aminobutyl)-2,5-diketopiperazine microparticles; wherein each of the microparticles has a specific surface area of 35 $m^2/g$ to about 67 $m^2/g$ and comprises an active agent.

2. The dry powder of claim 1, wherein the active agent is vasoactive agent, a neuroactive agent, an immunomodulating agent, a cytotoxic agent, an antibiotic, an antiviral agent, an antigen, and infectious agent, an inflammatory mediator, a hormone, or a cell surface antigen.

3. The dry powder of claim 1, wherein the active agent is a prostaglandin.

4. The dry powder of claim 3, wherein the prostaglandin is PG $I_2$.

5. The dry powder of claim 1, wherein the active agent is about 0.01% to about 20% of the weight of the microparticles.

6. A dry powder for inhalation comprising microparticles of a diketopiperazine of the formula:

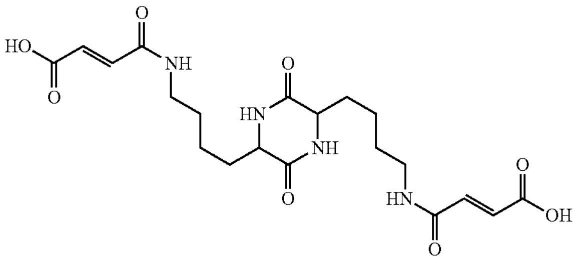 [SMILES: O=C(O)/C=C/C(=O)NCCCCC1NC(=O)C(CCCCNC(=O)/C=C/C(=O)O)NC1=O]

and a prostaglandin; wherein the microparticles have a specific surface area of 35 $m^2/g$ to about 67 $m^2/g$.

7. The dry powder of claim 6, wherein the prostaglandin is PG $I_2$ or an analog thereof.

8. A dry powder for inhalation comprising microparticles of a diketopiperazine of the formula:

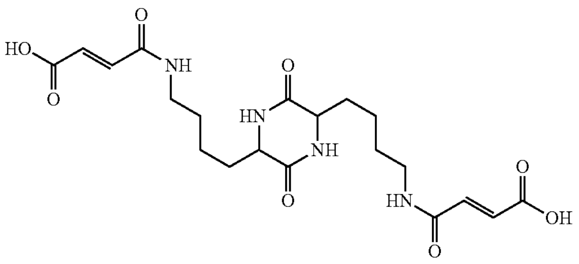 [SMILES: O=C(O)/C=C/C(=O)NCCCCC1NC(=O)C(CCCCNC(=O)/C=C/C(=O)O)NC1=O]

and granulocyte macrophage colony stimulating factor; wherein the microparticles have a specific surface area of 35 $m^2/g$ to about 67 $m^2/g$.

9. A dry powder inhaler comprising a dry powder formulation comprising microparticles of a fumaryl diketopiperazine (FDKP) having the formula:

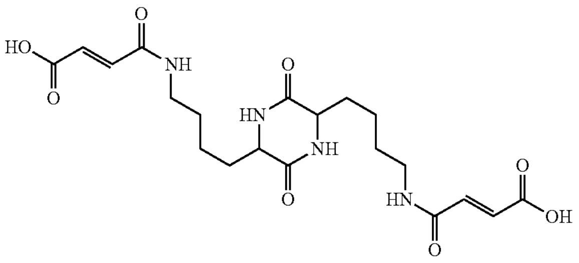 [SMILES: O=C(O)/C=C/C(=O)NCCCCC1NC(=O)C(CCCCNC(=O)/C=C/C(=O)O)NC1=O]

wherein the FDKP microparticles have a specific surface area of 35 $m^2/g$ to about 67 $m^2/g$ and one or more than one active agents.

10. The dry powder inhaler of claim 9, wherein the one or more active agents is a prostaglandin.

11. The dry powder inhaler of claim 10, wherein the one or more active agent prostaglandin PG 12 or an analog thereof.

12. The dry powder inhaler of claim 9 wherein the one or more active agent is granulocyte macrophage colony stimulating factor.

* * * * *